United States Patent

Westlund et al.

[11] Patent Number: 5,951,597
[45] Date of Patent: Sep. 14, 1999

[54] CORONARY SINUS LEAD HAVING EXPANDABLE MATRIX ANCHOR

[75] Inventors: Randy W. Westlund, Minneapolis; Bruce A. Tockman, Scandia; Ronald W. Heil, Jr., Roseville, all of Minn.

[73] Assignee: Cardiac Pacemakers, Inc., St. Paul, Minn.

[21] Appl. No.: 09/059,786

[22] Filed: Apr. 14, 1998

[51] Int. Cl.⁶ ...................................................... A61N 1/05
[52] U.S. Cl. .............................................................. 607/126
[58] Field of Search ..................................... 607/116, 122, 607/126; 128/899

[56] References Cited

U.S. PATENT DOCUMENTS

| | | |
|---|---|---|
| 5,514,380 | 5/1996 | Song et al. . |
| 5,531,783 | 7/1996 | Giele et al. ............................. 607/126 |
| 5,545,206 | 8/1996 | Carson .................................... 607/126 |
| 5,823,198 | 10/1998 | Jones et al. . |

OTHER PUBLICATIONS

"Effect of Water–Soluble Additves on Drug Release From Silicone Rubber Matrices. III. A Study of Release Mechanism by Differential Scanning Calorimetry"; V. Carelli et al. *International Journal of Pharmaceutics,* 30 (1986) 9–15.

"Effect of Water–Soluble Additives on Drug Release from Silicone Rubber Matrices. II. Sustained Release of Prednisolone From Non–Swelling Devices"; G. Di Colo, et al.; *International Journal of Pharmaceutics,* 30 (1986) 1–7.

"The Relationship Between Drug Release Rate, Particle Size and Swelling Of Silicone Matrices"; Gershon Golomb et al; *Journal Of Controlled Release,* 12 (1990) 121–132.

"Osmotic Effects in Water Absorption By Polymers"; R.F. Fedors, *Polymer,* 1980, vol. 21, Feb. 207–212.

*Primary Examiner*—William E. Kamm
*Attorney, Agent, or Firm*—Nikolai, Mersereau & Dietz, P. A.

[57] ABSTRACT

An intravenous lead for use with a cardiac device for implantation in the coronary venous system of the heart includes a lead body that is adapted to be routed through the vascular system into the coronary sinus with the distal end portion of the lead placed in the great cardiac vein or branch vein. The lead body includes a fixation member disposed just proximal of its tip. The fixation member comprises a radially expandable polymeric matrix that incorporates an osmotic agent so that when placed in a aqueous medium it will swell. Thus, when placed in a cardiac vein, the swelling of the fixation member will anchor the lead against longitudinal displacement due to body motion, blood flow and the beating action of the heart.

9 Claims, 1 Drawing Sheet

CORONARY SINUS LEAD HAVING EXPANDABLE MATRIX ANCHOR

BACKGROUND OF THE INVENTION

I. Field of the Invention

This invention relates generally to a cardiac pacing lead designed for placement in a coronary vein, and more particularly to such a lead employing as an anchoring device a radially expandable polymer matrix member for holding the distal end portion of the pacing lead carrying the stimulating electrode in place.

II. Discussion of the Prior Art

Cardiac pacemakers for treating bradycardia commonly employ pacing leads for connecting an electrical pulse generator to excitable cardiac tissue, usually within the heart's right ventricle. Such leads have one or more electrodes proximate the distal end thereof and also commonly employ tines located just distal of the tip electrode for holding that electrode in contact with endocardial tissue in the right ventricle. The tines engage the trabeculae, resisting movement of the lead tip due to body movement and/or contractions of the heart muscle itself.

More recently, researchers have found that cardiac stimulation can have a beneficial effect in treating patients suffering from congestive heart failure (CHF). By properly controlling the AV interval of the pacemaker, a sick heart may be made to pump more efficiently. Pacing therapy for the treatment of CHF, however, often requires the ability to stimulate the left ventricle, either alone or in conjunction with right ventricular stimulation. Current methods for achieving left ventricular pacing require placement of an epicardial lead, via thoracotomy or a thoracoscopic approach. Because of the usual poor condition of CHF patients, both of these procedures are "high risk" due to the trauma of the surgery itself and the need for general anesthesia. To obviate the need for a thoracotomy, left ventricular access (LVA) leads have been developed that may be introduced through the coronary sinus and then advanced through the coronary veins so that the lead's stimulating electrode can be positioned on the surface of the left ventricle near the apex of the heart.

Those skilled in the art knowing the anatomical configuration and dimensions of the coronary veins on the heart can appreciate that a lead to be routed therethrough must be of a relatively small diameter as compared to a conventional pacing lead adapted for placement in the right ventricle. Heart motion and respiratory motion as well as blood blow or other body movement are typical mechanisms for lead dislodgment. As such, a means must be provided for at least temporarily anchoring the electrode at a desired selected location until tissue ingrowth and resulting lead stabilization occurs. Additionally, a means must be provided to decouple the relative motion of the heart from the distal tip of the lead thereby reducing trauma to the coronary vein and neighboring myocardium. These problems are deemed to be more acute in CHF patients due to the dilated condition of CHF hearts and general diseased state of the tissue.

It can be seen, then, that a need exists for a pacing lead that can readily be advanced through the coronary sinus and thence through a coronary vein on the heart and having an anchoring and stress-relieving structure for safely maintaining the electrode at a desired site notwithstanding heart motion, respiratory motion blood flow and other body movement.

SUMMARY OF THE INVENTION

The present invention comprises an implantable lead for placement in a selected coronary vein. It includes a lead body with at least one electrode carried thereon at a distal end portion thereof and an elongated conductor contained within the lead body electrically joining a terminal pin at a proximal end of the lead body to the electrode at the distal end. To temporarily anchor the distal end portion of the lead body within the selected coronary vein until such time that tissue ingrowth can be relied upon for retention, the lead includes a fixation member that is located on the lead body proximal of the electrode for restraining displacement of the electrode where the fixation member comprises a water permeable, polymeric material incorporating an osmotically active agent that causes the polymeric material matrix to swell upon absorbing body fluids therein. The degree of swelling is sufficient to cause the fixation member to engage the wall of the coronary vein with sufficient force to inhibit longitudinal displacement of the lead body.

DESCRIPTION OF THE PREFERRED EMBODIMENT

Figure 1:
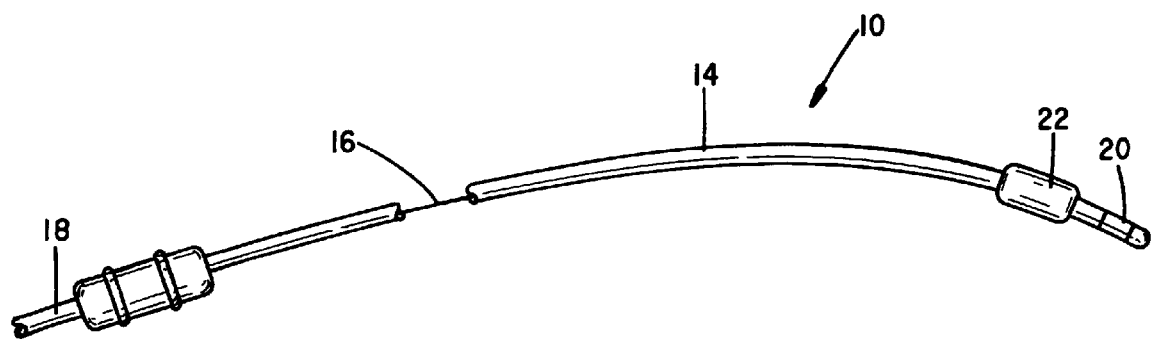
FIG. 1 is a partial view of a pacing lead designed for placement in the great cardiac vein or a branch vein on the left ventricle of the heart and incorporating expandable matrix anchoring device.

Referring to FIG. 1, there is indicated generally by numeral 10 a pacing lead specifically designed to be routed through the coronary sinus and into the great cardiac vein or a branch thereof traversing the epicardium of the left ventricle. The lead preferably comprises an elongated, flexible outer insulating polymer jacket 14 that surrounds an inner conductor 16. The conductor 16 extends the full length of the lead from its proximal terminal pin 18 to an electrode 20 affixed on the surface of the polymer jacket 14 near the distal end of the lead body.

In accordance with the present invention, there is located just proximal of the distal electrode 20 a fixation member 22. The fixation member comprises a water permeable, polymeric material incorporating within the polymer an osmotically active agent that swells or expands upon absorbing water from blood flowing in the vein in which the lead is placed. Without limitation, the water permeable polymer material may comprise silicone rubber and the osmotically active agent may comprise glycerol, sodium chloride, mannitol, potassium chloride, sodium phosphate or any other non-toxic, water soluble material that does not affect the curing of the water permeable polymer.

The polymeric matrix containing the osmotically active agent may be deposited onto the insulating elastomeric jacket 14 or, alternatively, the fixation member 22 may be pre-molded and subsequently affixed to the elastomeric jacket using a suitable adhesive.

Figure 2:
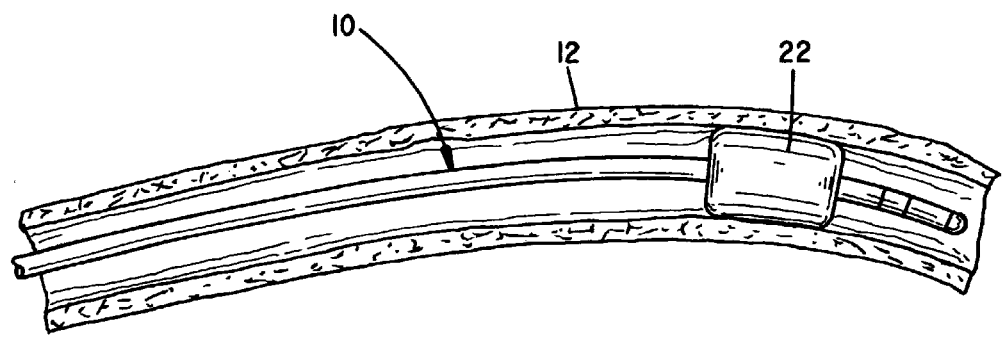
FIG. 2 is a partial cross-section view of a segment of a vein with the lead of the present invention anchored therein.

Referring to FIG. 2, a segment of a vein on the left side of the heart is identified by numeral 12 and the lead 10 incorporating the fixation member 22 is shown as having been advanced into the coronary vein 12. The fixation member 22 is illustrated in its swollen or expanded condition which allows it to engage the inside walls of the vein 12 to lodge the lead in place against longitudinal displacement.

The process by which the fixation member expands will now be described. As mentioned above, the fixation device consists generally of a silicone material or other suitable water permeable polymeric material containing at least one osmotically active agent, such as, but not restricted to, glycerol, sodium chloride, mannitol, potassium chloride, sodium phosphate or any other non-toxic, water soluble material that does not affect the curing of the water permeable polymer. Due to the presence of an osmotically active additive, the polymer-additive matrix naturally absorbs water upon contact with an aqueous fluid environment, e.g., blood. If allowed to remain in water contact, continued fluid ingress results in an increase in internal pressure and the polymer-additive matrix swells in physical size. A certain amount of the additive will be lost due to simple dissolution or rupture of fluid-filled cavities. This swelling process will continue until the osmotic agent is either consumed or until an equal amount of pressure is exerted inwardly on the polymer-additive matrix. The source of external pressure can be the mechanical strength of the polymer itself or some other surrounding structure, such as the vein wall. Once equalization of pressure occurs, the osmotic process is stopped and a state of equilibrium is achieved. The rate of expansion, generally, is determined by the polymer, the additive employed and the particle size of the additive.

Those skilled in the art can appreciate that once the lead is implanted, exposure to body fluids causes the fixation member 22 to swell against the vein lumen. Before such exposure, the fixation member 22 may be quite small in diameter, allowing the lead to be readily placed before swelling thereof is initiated. When exposed to body fluids for a sufficiently long time, the fixation member 22 may swell to nearly twice its original size. This method of fixation is quite unique in its approach in that the vessel 12 is capable of exerting sufficient pressure on the expandable fixation member 22 to arrest the osmotic process, thereby tailoring the size of the fixation member to the vessel itself. The process of expansion exerts forces against the vein walls to adequately secure the lead in the desired implant site.

In accordance with a further aspect of the invention, the fixation member 22 may comprise a resorbable polymer and may be bonded to the jacket 14 of the lead body using a resorbable polymer adhesive. This construction offers the benefit of a timely release of the fixation member 22 from the lead. Often, when cardiac pacing leads require extraction, it occurs within weeks of implantation. A resorbable adhesive can be formulated which would release the lead from the fixation member following a time sufficient for tissue encapsulation thereof to take place. The lead can then readily be withdrawn leaving the fixation member 22 behind. The fixation member 22 itself may be fabricated from a resorbable polymer such as polyvinylalcohol (PVO), polyethyleneoxide (PEO) or other suitable biodegradable hydrogel. In that way, the fixation member left behind upon removal of the lead would ultimately be absorbed by the body, but at a slower rate than the resorbable adhesive initially used for affixing fixation member 22 to the lead jacket 14.

As a further refinement of the invention, the active osmotic agent incorporated into the polymer matrix of the fixation member 22 may comprise an osmotic agent and a pharmacological agent. For example, an additive, such as dexamethasone sodium phosphate will provide osmotic activity to cause expansion of the fixation member 22 and therapeutic activity to improve electrode performance by lowering pacing thresholds. Other additives, such as calcium chloride, may be used not only to cause expansion of the fixation member, but to promote local blood coagulation.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. An electrical lead for applying cardiac stimulating pulses to the left ventricle of a patient's heart, comprising:
   (a) an elongated, flexible conductor contained within an insulating elastomeric jacket, the conductor terminating at an electrode proximate a distal end thereof and at an electrical terminal at a proximal end thereof; and
   (b) a fixation member located on the lead proximal of the electrode for restraining displacement of the electrode, the fixation member comprising a water-permeable polymeric material incorporating an osmotically active agent that swells upon absorbing body fluids therein.

2. The electrical lead as in claim 1 wherein the water-permeable polymeric material is silicone and wherein the osmotically active agent is selected from a group consisting of glycerol, sodium chloride, dexamethasone sodium phosphate, mannitol, potassium chloride and sodium phosphate.

3. The electrical lead as in claim 1 wherein the fixation member is deposited onto the insulating elastomeric jacket.

4. The electrical lead as in claim 1 wherein the fixation member is premolded and subsequently affixed to the elastomeric jacket.

5. The electrical lead as in claim 1 wherein the polymeric material is resorbable.

6. The electrical lead as in any one of claims 4 and 5 wherein the premolded fixation member is bonded to the elastomeric jacket with a resorbable adhesive.

7. The electrical lead as in claim 6 wherein the premolded fixation member is a resorbable polymeric material.

8. The electrical lead as in claim 7 wherein the resorbable polymeric material is selected from the group consisting of polyvinylalcohol, polyethyleneoxide and hydrogel multi-block copolymers.

9. The electrical lead as in claim 1 wherein the osmotically active agent comprises a pharmacologic agent.

* * * * *